United States Patent
Hoffmann et al.

(10) Patent No.: US 7,728,167 B2
(45) Date of Patent: Jun. 1, 2010

(54) PROCESS FOR THE PREPARATION OF ENANTIOMERICALLY ENRICHED AMINO ACIDS

(75) Inventors: Rolf Hoffmann, Hammersbach (DE); Michael Kraft, Rodenbach (DE)

(73) Assignee: Degussa AG, Dusseldorf (DE)

( * ) Notice: Subject to any disclaimer, the term of this patent is extended or adjusted under 35 U.S.C. 154(b) by 217 days.

(21) Appl. No.: 11/007,312

(22) Filed: Dec. 9, 2004

(65) Prior Publication Data

US 2005/0171359 A1    Aug. 4, 2005

(30) Foreign Application Priority Data

Dec. 10, 2003    (EP) .................................. 03028341

(51) Int. Cl.
*C07B 55/00*    (2006.01)
(52) U.S. Cl. ........................................ 562/401; 560/38
(58) Field of Classification Search .................. 562/401; 560/38
See application file for complete search history.

(56) References Cited

U.S. PATENT DOCUMENTS

| 6,235,927 B1 * | 5/2001 | Vries et al. .................. 562/401 |
| 6,372,936 B1 * | 4/2002 | Aikins et al. ................. 560/155 |
| 6,869,781 B2 | 3/2005 | Groger et al. ............... 435/106 |
| 2004/0029236 A1 | 2/2004 | Groger et al. ............... 435/106 |
| 2005/0142646 A1 | 6/2005 | Groger et al. ............... 435/106 |

FOREIGN PATENT DOCUMENTS

| DE | 102 20 740 A1 | 11/2003 |
| DE | 103 20 211 A1 | 12/2004 |
| WO | WO 03/016245 | 2/2003 |

OTHER PUBLICATIONS

Mandi, Ouafaa EI, Synthesis of New Seven-Membered Ring Cyclic Dipeptides From Functionalized Beta-Amino Acids, 2000, Eur. J. Org. Chem., pp. 251-255.*
Steer, David L., Beta-Amino Acids: Versatile Peptidomimetics, 2002, Current Medicinal Chemistry, 9, pp. 811-822.*
Izumi, et al., "Herstellung und Verwendung von Aminosauren," *Angew. Chem.* 90:187-194 (1978).
English translation of Izumi, et al. article, Reference C1 above.
English language abstract for DE 102 20 740 A1, Reference B2 above.
English language abstract for DE 103 20 211 A1, Reference B3 above.

* cited by examiner

*Primary Examiner*—Daniel M Sullivan
*Assistant Examiner*—Sudhakar Katakam
(74) *Attorney, Agent, or Firm*—Law Office of: Michael A. Sanzo, LLC

(57) ABSTRACT

The present invention is concerned with the resolution of a mixture of enantiomers of N-protected amino acids by crystallization with enantiomerically pure N-unprotected β-amino acid derivatives.

17 Claims, No Drawings

PROCESS FOR THE PREPARATION OF ENANTIOMERICALLY ENRICHED AMINO ACIDS

CROSS REFERENCE TO RELATED APPLICATIONS

The present application claims priority to European application EP 03 028 341.0, filed on Dec. 10, 2003, the contents of which is hereby incorporated by reference.

FIELD OF THE INVENTION

The present invention is concerned with a process for the resolution of a mixture of enantiomers of N-protected amino acids, preferably α-amino acids. The process involves crystallisation of a diastereomeric salt pair consisting of one enantiomer of an N-protected amino acid and an enantiomerically pure N-unprotected β-amino acid derivative.

BACKGROUND OF THE INVENTION

Enantiomerically enriched amino acids, especially α-amino acids, are useful in the synthesis of enantiomerically pure bio-active compounds, as intermediates for pharmaceuticals and for inclusion in infusion liquors for parenteral nutrition. Large quantities of these amino acids, especially L-lysine, are also produced for feed additive compositions.

The resolution of mixtures of enantiomers of amino acids, e.g., racemates, via classical crystallisation techniques is a common method for the generation of enantiomerically enriched amino acids. Although there have been great efforts to create new methodologies which allow the synthesis of amino acids in pure form e.g. using biotechnology, the classical pathway is still of value for special amino acids which are not, or only poorly, generated by biotechnological methods (Izumi et al., *Angew. Chem.* 90:187 (1978); Hoppe, et al., *Chemie in unserer Zeit* 18:73 (1984)).

SUMMARY OF THE INVENTION

The objective of the present invention is to create a process for resolving enantiomeric mixtures of N-protected amino acids (preferably α-amino acids or β-amino acids, with α-amino acids being most preferred). This objective is achieved by crystallizing the salt of one enantiomer of the N-protected amino acid with an enantiomerically pure N-unprotected β-amino acid derivative, preferably an ester of the amino acid. The process is feasible even on large scale and allows enantiomerically enriched amino acids to be made in an easy and robust way.

The process is carried out in an organic solvent which can, optionally, contain water to the extent that it does not adversely affect crystallisation, e.g., through phase separation. The solvent should generally be a polar one, preferably selected from the group consisting of esters, ethers, ketones, alcohols, aromatic hydrocarbons or mixtures thereof. Especially preferred is a process in which the solvent is selected from the group consisting of ethyl acetate, ethanol, methyl-tert.-butyl ether, and toluene.

The enantiomerically pure N-unprotected β-amino acid derivative used as resolving agent may be chosen after carrying out routine tests of derivatives in the process and comparing the results obtained. These enantiomerically pure amino acids are commercially available or can be made according to processes known in the art (see e.g., DE10220740 or DE10320211 and literature cited therein). The generation of derivatives such as esters or amides, from these amino acids may be carried out using procedures well known in the art (Chemistry of Amino Acids, Wiley & Sons 1961, J. P. Greenstein, M Winitz).

Preferred enantiomerically pure N-unprotected β-amino acid derivatives are those of formula (I) or (II):

wherein:

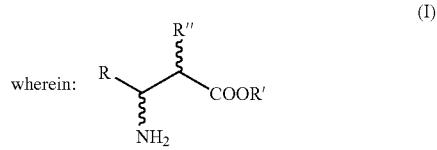

$R^1$ and $R^2$ independently of one another are H or R;

R and R' independently of one another are: $(C_1-C_8)$-alkyl, $(C_2-C_8)$-alkoxyalkyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{18})$-heteroaryl, $(C_3-C_8)$-cycloalkyl, $(C_1-C_8)$-alkyl-$(C_3-C_8)$-cycloalkyl, or $(C_3-C_8)$-cycloalkyl-$(C_1-C_8)$-alkyl;

R" is HO—, $(C_1-C_8)$-alkyl, $(C_2-C_8)$-alkoxyalkyl, $(C_6-C_{18})$-aryl, $(C_7-C_{19})$-aralkyl, $(C_3-C_{18})$-heteroaryl, $(C_4-C_{19})$-heteroaralkyl, $(C_1-C_8)$-alkyl-$(C_6-C_{18})$-aryl, $(C_1-C_8)$-alkyl-$(C_3-C_{18})$-heteroaryl, $(C_3-C_8)$-cycloalkyl, $(C_1-C_8)$-alkyl-$(C_3-C_8)$-cycloalkyl, or $(C_3-C_8)$cycloalkyl-$(C_1-C_8)$-alkyl;

or R and R"; R and R'/$R^1$; or R' and R'/$R^1$ represent a $(C_3-C_5)$-alkylene bridge mono- or polysubstituted with $(C_1-C_8)$-alkyl, HO—$(C_1-C_8)$-alkyl, $(C_1-C_8)$-alkoxy, $(C_2-C_8)$-alkoxyalkyl, $(C_6-C_{18})$-aryl, $(C_7-C_{19})$-aralkyl, $(C_1-C_8)$-alkyl-$(C_6-C_{18})$-aryl, $(C_3-C_8)$-cycloalkyl, $(C_1-C_8)$-alkyl-$(C_3-C_8)$-cycloalkyl, $(C_3-C_8)$-cycloalkyl-$(C_1-C_8)$-alkyl.

Especially, preferred are esters of β-amino acids. Preferably aromatic esters like 3-amino-3-phenylpropionic acid ethyl ester or the respective amide.

The temperature applied during the crystallisation process should be chosen to allow maximum yield with an optimum enantiomeric excess of the N-protected amino acid. The temperature is preferably held within a range of −30° to 100° C. More preferably the temperature is −25 to 50° C., and most preferred it is between −20° C. and 30° C.

After crystallisation the mixture is worked-up using methods routine in the art. One preferred method is to separate the solid material from the mixture via filtration. Subsequently the highly enriched diastereomeric salt pair can be recrystallized to maximise diastereomeric purity. Afterwards the enantiomerically enriched N-protected amino acid can be liberated from this salt by standard methods, e.g., ion-exchange or classical acidification and extraction techniques.

It is possible to exchange substrates and crystallising agent for each other to create a process for obtaining enantiomerically enriched N-unprotected β-amino acids. Hence, the present invention also concerns a process for the preparation of enantiomerically enriched N-unprotected β-amino acid derivates in which a mixture of both enantiomers of an N-unprotected β-amino acid derivative is resolved through crystallisation of the salt of one enantiomer of the N-unprotected β-amino acid derivative with an enantiomerically pure N-protected α-amino acid. Preferred embodiments of this process are in line with those mentioned for performing the process for the preparation of N-protected amino acids.

The present invention can be performed, for example, by dissolving the racemic N-protected amino acid in an appropriate solvent. Upon total dissolution, the enantiomerically pure N-unprotected β-amino acid derivative, especially the ester, is added in an amount sufficient to obtain optimal crystallisation results in view of yield and diastereomeric purity. The molar ratio of added enantiomerically pure N-unprotected β-amino acid derivative to the antipode of N-protected amino acid to be crystallised can vary from 1:0.1 to 1:2, preferably from 1:0.5 to 1:1.8 and most preferably from 1:0.7 to 1:1.5. Preferably after cooling and completion of crystallisation, the solid material is separated via filtration from the mixture and optionally recrystallized. Liberation of the desired N-protected amino acid takes place preferably through acidification and extraction.

The process can be applied to the production of β-amino acid derivates, as described above except that N-protected amino acids have to be substituted for N-unprotected β-amino acid derivates and vice versa.

DEFINITIONS

As used herein, the term "N-protected amino acid" means any carboxylic acid having both a carboxyl-function and a protected amino-function within one molecule. Preferably an α-amino acid protected by a common protective group at the α-nitrogen atom of the amino acid is used. Suitable protective groups are known to the skilled worker (Green et al. Protective Groups in Organic Chemistry, Wiley&Sons, 1981). Preferred residues are selected from the group consisting of Z-, Boc-, Moc-, Eoc-, Fmoc-, formyl-, acetyl-, and phthaloyl-radicals.

The term "α-amino acid" denotes a naturally or unnaturally occurring amino acid such as that depicted in Bayer-Walter, *Lehrbuch der organischen Chemie*, S. Hirzel Verlag, Stuttgart, 22. Auflage, S. 822 et seq. Unnatural amino acids are those mentioned, for example, in DE19903268.8. The most preferred of these is N-protected tert.-leucine.

Methyl, ethyl, n-propyl, isopropyl, n-butyl, isobutyl, sec-butyl, tert-butyl, pentyl, hexyl, heptyl or octyl, together with all their bond isomers, are $(C_1-C_8)$-alkyl radicals.

The $(C_1-C_8)$-alkoxy radical corresponds to the $(C_1-C_8)$-alkyl radical, with the proviso that this is bonded to the molecule via an oxygen atom.

The term $(C_2-C_8)$-alkoxyalkyl, refers to a radical in which the alkyl chain is interrupted by at least one oxygen and in which two oxygen atoms are not joined to one another. The number of carbon atoms gives the total number of carbon atoms contained in the radical.

The term "$(C_3-C_5)$-alkylene bridge" refers to a carbon chain with three to five C atoms, this chain being bonded to the molecule in question via two different C atoms. The bridge optionally can be unsaturated and/or can contain one or more heteroatoms like N, O, or S within the chain.

The radicals described above can be mono- or polysubstituted with $(C_1-C_8)$-alkoxy, $(C_1-C_8)$-alkyl, halogens and/or radicals containing N, O, P, S or Si atoms. These are particularly alkyl radicals of the type mentioned above having one or more of these heteroatoms in their chain or being bonded to the molecule via one of these heteroatoms.

"$(C_3-C_8)$-cycloalkyl" means cyclopropyl, cyclobutyl, cyclopentyl, cyclohexyl or cycloheptyl radicals etc. These can be substituted with one or more halogens and/or radicals containing N, O, P, S or Si atoms and/or can have N, O, P or S atoms in the ring, such as e.g., 1-, 2-, 3-, 4-piperidyl, 1-, 2-, 3-pyrrolidinyl, 2-, 3-tetrahydrofuryl, 2-, 3-, 4-morpholinyl.

"$(C_3-C_8)$-cycloalkyl-$(C_1-C_8)$-alkyl radical" refers to a cycloalkyl radical as set out above, which is bonded to the molecule via an alkyl radical as stated above.

For the purposes of the present invention, "$(C_1-C_8)$-acyloxy" means an alkyl radical as defined above with a maximum of 8 C atoms, which is bonded to the molecule via a COO— function.

$(C_1-C_8)$-Acyl within the framework of the invention means an alkyl radical as defined above with a maximum of 8 C atoms, which is bonded to the molecule via a CO-function.

"$(C_6-C_{18})$-aryl radical" is understood to mean an aromatic radical with 6 to 18 C atoms. These include, in particular, compounds such as phenyl, naphthyl, anthryl, phenanthryl or biphenyl radicals, or systems of the type described above annelated to the molecule in question, such as e.g., indenyl systems, which can optionally be substituted with $(C_1-C_8)$-alkyl, $(C_1-C_8)$-alkoxy, $(C_1-C_8)$-acyl or $(C_1-C_8)$-acyloxy.

For the purposes of the present invention, A "$(C_7-C_{19})$-aralkyl radical" is a $(C_6-C_{18})$-aryl radical bonded to the molecule via a $(C_1-C_8)$-alkyl radical.

A "$(C_3-C_{18})$-heteroaryl radical" refers to a five-, six- or seven-membered aromatic ring system of 3 to 18 C atoms, which contains heteroatoms such as nitrogen, oxygen or sulfur in the ring. In particular, radicals such as 1-, 2-, 3-furyl, such as 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl and 2-, 4-, 5-, 6-pyrimidinyl are considered as such heteroaromatics.

"$(C_4-C_{19})$-heteroaralkyl" means a heteroaromatic system corresponding to the $(C_7-C_{19})$-aralkyl radical.

Fluorine, chlorine, bromine and iodine are suitable halogens (Hal) for use in the invention.

For the purposes of the present invention, the term "enantiomerically enriched" means that a proportion of an enantiomer in a mixture with its optical antipode, wherein the enantiomer is present in a range of >50% and <100%. The ee (enantiomeric excess) value is calculated as: ([Enantiomer1]-[Enantiomer2])/([Enantiomer1]+[Enantiomer2])=ee value.

The term "diastereomerically enriched" or "diastereomeric purity" is the proportion of one diastereomer in a mixture with its other diastereomers in a range, wherein, in an enriched preparation, one diastereomer is in the range of >50% and <100%.

Unless otherwise indicated the names of molecules and groups are intended to include all possible diastereomers, the two optical antipodes of any diastereomer also being included.

EXAMPLES

Example 1

A solution of 59.9 g Benzyloxycarbonylphenylalanine in ethyl acetate was treated with 60 g (R)-3-Amino-3-phenyl-propionic acid ethyl ester in ethyl acetate at 35° C., cooled to 0° C. and stirred for 40 h. After filtration and drying 30.5 g of a 1:1 salt of R-Benzyloxycarbonylphenylalanine×(R)-3-Amino-3-phenylpropionic acid ethyl ester (86:14 optical purity) was obtained.

Example 2

A solution of 50.2 g Benzyloxycarbonylvaline in methyl-tert.-butyl ether was treated with 60 g (S)-3-Amino-3-phenyl-propionic acid ethyl ester in methyl-tert.-butyl ether at 30° C., cooled to 0° C. and stirred for 30 h. After filtration and drying 27.1 g of a 1:1 salt of (S)-Benzyloxycarbonylvaline×(S)-3-Amino-3-phenylpropionic acid ethyl ester (97:3 optical purity) was obtained.

Example 3

A solution of 47.6 g Benzyloxycarbonylamino-butyric acid in methyl-tert.-butyl ether was treated with 21.3 g (S)-3-Amino-3-phenylpropionic acid ethyl ester in methyl-tert.-butyl ether at 30° C., cooled to 10° C. and stirred for 10 h. After filtration and drying 45.1 g of a 1:1 salt of (S)-Benzyloxycarbonylamino-butyric acid×(S)-3-Amino-3-phenylpropionic acid ethyl ester (92:8 optical purity) was obtained.

Example 4

A solution of 106.1 g Benzyloxycarbonylamino-tert.leucine in methyl-tert.-butyl ether was treated with 42.56 g (R)-3-Amino-3-phenylpropionic acid ethyl ester in methyl-tert.-butyl ether at 35° C., cooled to 0° C. and stirred for 15 h. After filtration and drying 71.8 g of a 1:1 salt of (R)-Benzyloxycarbonylamino-butyric acid×(R)-3-Amino-3-phenylpropionic acid ethyl ester (97:3 optical purity) was obtained.

Example 5

A solution of 59.9 g Benzyloxycarbonylamino-tert.-leucine in ethyl acetate was treated with 60 g (R)-3-Amino-3-phenylpropionic acid ethyl ester in ethyl acetate at 42° C., cooled to −10° C. and stirred for 10 h. After filtration and drying 38.5 g of a 1:1 salt of (R)-Benzyloxycarbonylamino-tert.-leucine×(R)-3-Amino-3-phenylpropionic acid ethyl ester (98.8:1.2 optical purity) was obtained.

After recrystallization all salt pairs were obtained in an optical purity of >99:1.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A process for the preparation of an enantiomerically enriched N-protected amino acid from a mixture of both enantiomers, comprising crystallizing the salt of one enantiomer of the N-protected amino acids with an enantiomerically pure N-unprotected β-amino acid derivative to form a diastereomeric salt pair consisting of one enantiomer of said N-protected amino acid and said enantiomerically pure N-unprotected β-amino acid derivative, and wherein the desired N-protected amino acid is recovered from said diastereomeric salt pair,
   wherein N-protected amino acid is selected from benzyloxycarbonylphenylalanine, benzyloxycarbonylvaline, benzyloxycarbonylamino-butyric acid, benzyloxycarbonylamino-tert.leucine, and
   wherein N-unprotected β-amino acid is selected from (R)-3-amino-3-phenylpropionic acid ethyl ester and (S)-3-amino-3-phenylpropionic acid ethyl ester.

2. The process of any one of claim 1, wherein the crystallised salt is separated from the mixture by filtration.

3. The process of any one of claim 1, wherein the crystallisation is performed in a polar solvent.

4. The process of claim 3, wherein the temperature during crystallisation is between −20° C. and 30° C.

5. A process for the preparation of an enantiomerically enriched N-protected amino acid from a mixture of both enantiomers, comprising crystallizing the salt of one enantiomer of the N-protected amino acid with an enantiomerically pure N-unprotected β-amino acid derivative, wherein said enantiomerically pure N-unprotected β-amino acid derivative is the sole resolving agent used in said process, and wherein the desired N-protected amino acid is recovered from said diastereomeric salt pair,
   wherein N-protected amino acid is selected from benzyloxycarbonylphenylalanine, benzyloxycarbonylvaline, benzyloxycarbonylamino-butyric acid, benzyloxycarbonylamino-tert.leucine, and
   wherein N-unprotected n-amino acid is selected from (R)-3-amino-3-phenylpropionic acid ethyl ester and (S)-3-amino-3-phenylpropionic acid ethyl ester.

6. The process of claim 1, wherein N-protected amino acid is benzyloxycarbonylphenylalanine.

7. The process of claim 1, wherein N-protected amino acid is benzyloxycarbonylvaline.

8. The process of claim 1, wherein N-protected amino acid is benzyloxycarbonylamino-butyric acid.

9. The process of claim 1, wherein N-protected amino acid is benzyloxycarbonylamino-tert.leucine.

10. The process of claim 1, wherein N-unprotected β-amino acid is (R)-3-amino-3-phenylpropionic acid ethyl ester.

11. The process of claim 1, wherein N-unprotected β-amino acid is (S)-3-amino-3-phenylpropionic acid ethyl ester.

12. The process of claim 5, wherein N-protected amino acid is benzyloxycarbonylphenylalanine.

13. The process of claim 5, wherein N-protected amino acid is benzyloxycarbonylvaline.

14. The process of claim 5, wherein N-protected amino acid is benzyloxycarbonylamino-butyric acid.

15. The process of claim 5, wherein N-protected amino acid is benzyloxycarbonylamino-tert.leucine.

16. The process of claim 5, wherein N-unprotected β-amino acid is (R)-3-amino-3-phenylpropionic acid ethyl ester.

17. The process of claim 5, wherein N-unprotected β-amino acid is (S)-3-amino-3-phenylpropionic acid ethyl ester.

* * * * *